United States Patent [19]

Pill et al.

[11] Patent Number: 5,641,810

[45] Date of Patent: Jun. 24, 1997

[54] USE OF α, ω-DICARBOXYLIC ACIDS AS FIBRINOGEN SINKERS

[75] Inventors: Johannes Pill, Leimen; Liesel Doerge, Mannheim; Karlheinz Stegmeier, Heppenheim, all of Germany

[73] Assignee: Boehringer Mannheim GmbH, Germany

[21] Appl. No.: 373,264

[22] PCT Filed: Jul. 17, 1993

[86] PCT No.: PCT/EP93/01894

§ 371 Date: Jan. 25, 1995

§ 102(e) Date: Jan. 25, 1995

[87] PCT Pub. No.: WO94/02128

PCT Pub. Date: Feb. 3, 1994

[30] Foreign Application Priority Data

Jul. 25, 1992 [DE] Germany ............ 42 24 670.9

[51] Int. Cl.[6] .................................................. A61K 31/20
[52] U.S. Cl. .................................... 514/558; 514/574
[58] Field of Search .................................. 514/558, 574

[56] References Cited

U.S. PATENT DOCUMENTS 4,908,385  3/1990  Bar-Tana et al. .................. 514/574

*Primary Examiner*—James J. Seidleck
*Assistant Examiner*—John M. Cooney, Jr.
*Attorney, Agent, or Firm*—Nikaido Marmelstein Murray & Oram LLP

[57] ABSTRACT

Compounds of α,ω-dicarboxylic acids of the formula I

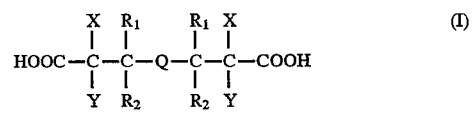

in which X and Y, which can be the same or different, signify hydrogen, halogen, $C_1$–$C_6$-alkyl, $C_1$–$C_6$-alkoxy, hydroxyl, cyano, carboxyl, $C_1$–$C_6$-alkoxycarbonyl or carbamoyl, $R_1$ and $R_2$, which can be the same or different, hydrogen or $C_1$–$C_6$-alkyl and Q a linear saturated or unsaturated alkylene chain with 2–14 C-atoms in which one or more C-atoms can be replaced by cyclohexyl rings, phenyl or heterocycles, as well as of their in vivo-hydrolysable carboxylic acid derivatives for the preparation of medicaments with fibrinogen-lowering action.

6 Claims, No Drawings

USE OF α, ω-DICARBOXYLIC ACIDS AS FIBRINOGEN SINKERS

The present invention concerns the use of α, ω-dicarboxylic acids for the preparation of medicaments for the prevention and treatment of fibrinogen-mediated obstructive occurrences in blood vessels.

Fibrinogen is a glycoprotein in the blood which plays an essential part in haemostasis and maintenance of the blood viscosity. It participates in the formation of platelet aggregates and in the coagulation cascade. By means of thrombin, fibrinogen is converted into fibrin monomers which, after polymerisation, form the basis for haemostatic occlusions.

Besides other things, fibrinogen is an independent risk factor (J. Inter. Med., 227, 365–373, 1990) for cardiovascular diseases, as has been shown in various large prospective clinical studies (summarised in TiPS, 11, 444–451, 1990). Increased plasma fibrinogen levels are frequently associated with a dyslipidaemia but also with peripheral vascular occlusive disease, hypertension and diabetes (J. Am. Med. Assoc., 258, 1193–1186, 1987; J. Am. Med., 85, 584–585, 1988). The occulsion rate after by-pass operations is also correlated with the level of the plasma fibrinogen (Brit. Med. J., 199, 643–646, 1989). It is generally accepted that increased fibrinogen levels lead to morphological changes in the blood vessels and are not a result of these (J. Intern. Med., 227, 365–373, 1990).

Active materials which lead to a lowering of the plasma fibrinogen are, therefore, of therapeutic value in a number of pathological states.

The task forming the basis of the present invention is to make available suitable medicaments which can be used for the treatment of hyperfibrinogenaemia.

In the scope of the present invention, it has now, surprisingly, been found that α, ωdicarboxylic acids of the following formula I lead to a lowering of the fibrinogen in the plasma of various animal species or mitigate the increase of fibrinogen in blood plasma after stimulation. Therefore, the substances are suitable for the treatment or prevention of hyperfibrinogenaemias as a result of which obstructive blood vessel diseases arise, such as e.g. in the case of arteriosclerotic changes, diseases of the venous system resulting in thrombotic and embolic complications or hyperfibrinogenaemias after angioplastic procedures and inflammatory or neoplastic processes.

The subject of the present invention are α,ω-dicarboxylic acids of the general formula I

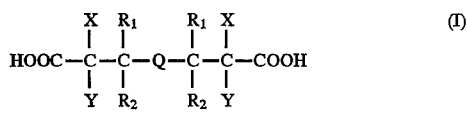

in which X and X, which can be the same or different, signify hydrogen, halogen, $C_1$–$C_6$-alkyl, $C_1$–$C_6$-alkoxy, hydroxyl, cyano, carboxyl, $C_1$–$C_6$-alkoxycarbonyl or carbamoyl, $R_1$ and $R_2$, which can be the same or different, hydrogen or $C_1$–$C_6$-alkyl and Q a linear saturated or unsaturated alkylene chain with 2–14 C-atoms in which one or more C-atoms can be replaced by cycloalkyl rings, phenyl or heterocycles, as well as their in vivo-hydrolysable carboxylic acid derivatives.

Preferred are compounds of the formula I in which X and Y, which can be the same or different, signify hydrogen or halogen, $R_1$ and $R_2$, which can be same or different, hydrogen or methyl and Q a linear chain with 2–14 C-atoms, a —$(CH_2)_n$-cyclohexylidene-$(CH_2)_n$—, a —$(CH_2)_m$-phenylene-$(CH_2)_m$—, a —$CH_2$—$CH$=$CH$-phenylene—$CH$=$CH$—$CH_2$— or a —$CH_2$—$CH$=$CH$—$CH_2$-phenylene-$CH_2CH$=$CH$—$CH_2$— group, whereby n represents the numbers 2, 3 or 4 and m the numbers 3 or 4, as well as their in vivo-hydrolysable carboxylic acid derivatives.

Especially preferred are the two compounds of the formula I in which X and Y each signify hydrogen, $R_1$ and $R_2$ each a methyl group and Q a —$(CH_2)_{10}$— group (compound A) and X and Y each chlorine, $R_1$ and $R_2$ each hydrogen and Q a —$(CH_2)_8$— group (compound B).

By halogen in the case of the meaning of X and Y, respectively, is to be understood fluorine, chlorine or bromine, especially chlorine or bromine.

Cycloalkyl rings are carbocyclic rings with 3–7 C-atoms, the cyclohexyl ring being preferred.

Heterocycles are preferably piperidine, piperazine and pyrrolidine rings.

The phenyl, cyclohexyl, piperidine as well as the piperazine ring system of the chain Q can be incorporated into the chain via the 1,2-, 1,3- or 1,4-position.

α, ω-Dicarboxylic acids of the formula I are the subject of the Patent Applications EP-A-81 930, EP-A-185 080 and EP-A-279 978 in which the compounds are described as medicaments for the treatment of obesity, hyperlipidaemia or diabetes.

The compounds of the formula I are prepared according to the processes described in the cited Patent Applications.

The pharmacological investigations with regard to the fibrin-lowering action are carried out, for example, for the claimed α,ω-dicarboxylic acids with the above-mentioned compounds A and B.

For the treatment and prevention of a hyperfibrinogenaemia for the prevention of occlusive blood vessel diseases, α,ω-dicarboxylic acids are administered systemically, preferably enterally, especially preferably orally but also parenterally (i.v.). The dosage varies according to the requirements of the individual patient as have been determined by the physician providing the treatment. For compound B, in general a daily dosage of about 100–1000 mg should be used. On the basis of animal experimental data, this dosage range can be regarded as sufficient. For the prevention of a re-stenosis after angioplasty, the α,ω-dicarboxylic acid should preferably be administered before the intervention and thereafter until the risk of a re-stenosis has become negligible. In this connection, it is also to be pointed out that, because of the possibility of oral administration of the α,ω-dicarboxylic acids, a period of treatment is not chronologically limited, which is of importance for the use according to the invention.

As forms of administration, there come into consideration the solid or liquid forms of administration usual for systemic administration, e.g. suppositories, or, as solid oral forms of administration, capsules, tablets, film-coated tablets, dragees, pills, powders, granulates and the like, as liquid oral forms of administration solutions, syrups, suspension, elixirs and the like and as parenteral forms of administration infusion or injection solutions which can be injected i.v. or i.m.

Within the scope of the present invention, the α,ω-dicarboxylic acids can be incorporated into the enteral or oral forms of administration in any amount suitable for the administration. However, it is preferred to produce compositions which, per dosage unit, contain the active material in an amount of up to 1000 mg, preferably of about 100–400 mg. Especially preferred is the production of capsules, tablets and film-coated tablets as dosage units. These can be administered one or more times per day according to requirements to be ascertained by the physician.

The production of the above-mentioned forms of use can be carried out e.g. on the basis of the following example for compound B.

Example 1: Production of a tabletting or capsule filling mass

Tablets with 200 mg of compound B

| composition | mg/capsule |
| --- | --- |
| 1. compound B | 200.0 |
| 2. lactose × 1H$_2$O | 50.0 |
| 3. crospovidone | 10.0 |
| 4. povidone 25,000 | 10.5 |
| 5. crospovidone | 5.0 |
| 6. silicon dioxide colloidal | 2.5 |
| 7. cellulose microcrystalline | 20.0 |
| 8. magnesium stearate | 5.0 |
| filling weight | 303.0 |
| 9. gelatine capsules | size 0 |

The components are mixed with one another according to conventional processes and moist or dry granulated. The final mass can be pressed to give cores and used directly as tablets or as film tablets coated with a film. The mass can also be filled directly into capsules, such as e.g. gelatine capsules.

Example 2: Therapeutic action

The therapeutic action of compound A and compound B for the lowering of fibrinogen in blood plasma can be seen from the following experiments. The experiments are so described that anybody with the necessary knowledge and apparatus can carry them out. By the choice of the described experiments, it is not intended to limit in any way the scope of the use of the invention.

1a) General principle

The administration of turpentine i.m. leads, in the case of the rat, to a drastic increase of the fibrinogen in the plasma after 24 hours (168 to 490 mg/100 ml). This increase is essentially caused by an increase of the endogenic synthesis (Clin. Hemorheol., 11, 465–477, 1991). A substance action can be well demonstrated by a mitigation of the turpentine-caused hyperfibrinogenaemia.

1b) Description of the experiment

Over the course of 4 days, male Sprague-Dawley rats received compound A or B in a dosage of 25 mg/kg/d in 1% tylose suspension. The controls received the same amount of the vehicle. On the 4th day, immediately before the substance administration, blood was taken from the tail vein for the determination of the fibrinogen. In addition, 1 ml of turpentine/kg was administered i.v. 24 hours after administration of turpentine, blood was again taken from the tail vein for the determination of fibrinogen.

1c) Results

Whereas, in the case of the solvent-treated controls, the fibrinogen in the blood plasma increased, on average, by 322 mg/100 ml (n=6), in the case of animals treated with compound B or compound A, there was found an increase of 222 and 225 mg/100 ml, respectively (n=12 and 6, respectively).

2a) General principle

Genetically hypercholesterolaemic rabbits which spontaneously develop an atherosclerosis have increased plasma fibrinogen levels (Thromb. Haemost., 61, 140–143, 1989). We investigated whether compound B leads in these animals, in comparison with other lipid-lowering substances, such as probucol and mevinolin, to a lowering of the fibrinogen in the plasma.

2b) Description of the experiment

Male genetically hypercholestrolaemic (WHHL) rabbits received, over a period of time of 8 weeks, feed which had been admixed with 0.33% of mevinolin. The control animals received substance-free feed. Blood for the fibrinogen determination was taken from the central ear artery of the animals immediately before as well as after an 8 week treatment.

2c) Results

In the following Table 1 are given the fibrinogen concentrations in the blood plasma before commencement of the treatment and after an 8 week treatment. The animals treated with compound B show a statistically significantly lower fibrinogen level in the plasma, whereas the control animals, as well as those treated with probucol and mevinolin, showed, on average, slightly higher values.

| | Fibrinogen [mg/100 ml] | |
| --- | --- | --- |
| | initial value | 8 weeks |
| control | 265 ± 26.1 | 279 ± 37.0 |
| | (n = 7) | (n = 7) |
| compound B | 258 ± 26.6 | 122 ± 27.3[+] |
| [0.33%] | (n = 6) | (n = 6) |
| probucol | 248 ± 18.9 | 276 ± 32.1 |
| [1%] | (n = 7) | (n = 7) |
| mevinolin | 245 ± 13.7 | 309 ± 29.8 |
| [0.033%] | (n = 7) | (n = 7) |

[+]p < 0.01, U test unpaired

Tab.: Fibrinogen in the plasma of genetically hypercholesterolaemic rabbits before and after 8 weeks of treatment with compound B, probucol and mevinolin as admixture to the feed with the amounts given in square brackets (x±SD).

3a) General principle

For the evaluation of transferability of fibrinogen lowering of compound B observed in the case of rats and rabbits to other species, fibrinogen was determined in dogs after 3 months substance treatment.

3b) Description of the experiment

Male beagles received compound B in doses of 7, 15 and 35 mg/kg/d in the form of ovuls over a period of time of 3 months. At the end of the treatment, blood was taken from the veins of the front legs for the determination of fibrinogen.

3c) Results

From the following Table, it can be seen that, already at a dose of 7 mg/kg/d, compound B leads in the case of the dog to a statistically significant lowering of the fibrinogen in the blood plasma. The further increase of the dose of compound B to 15 or 35 mg/kg/d does not lead to an increase of the fibrinogen lowering.

| Fibrinogen [mg/100 ml] | |
| --- | --- |
| control | 218 ± 27.9 |
| compound B mg/kg/d | |
| 7 | 167 ± 13.1[+] |
| 15 | 161 ± 12.1[+] |
| 35 | 167 ± 16.7[+] |

Tab.: Fibrinogen in the blood plasma of male beagles after 3 months peroral administration of compound B in doses of 7, 15 and 35 mg/kg/d in the form of ovuls (x±SD, n=5, [+]p<0.01, U test unpaired)

The results here set out clearly demonstrate that α,ω-dicarboxylic acids possess a fibrinogen-lowering action. As comparative investigations with the lipid sinkers probucol and mevinolin show, this effect is not to be ascribed to the already-described hypolipidaemic action of α,ω-dicarboxylic acids but rather represents a new quality of action of this class of substances.

We claim:

1. A method of preventing and/or treating fibrinogen-mediated obstructed occurrences of blood vessels in a patient in need thereof, the method comprising administering to the patient a fibrinogen-mediated obstructive occurrence preventing or treating-effective amount of the compound of the formula I

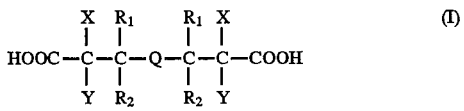

wherein X and Y are both hydrogen, $R_1$ and $R_2$ are both methyl and Q is —$(CH_2)_{10}$—, or X and Y are both chlorine, $R_1$ and $R_2$ are each hydrogen and Q is —$(CH_2)_8$—.

2. Method of claim 1, wherein the method reduces fibrinogen in the blood of the patient.

3. Method of claim 1, wherein the method prevents and/or treats hyperfibrinogenaemia.

4. Method of claim 1, wherein the method prevents fibrinogen-mediated blood vessel changes.

5. Method of claim 1, wherein the method is a method for the prevention or alleviation of fibrinogen-associated disease.

6. A method of reducing fibrinogen in the blood plasma of a patient, or of mitigating the increase of fibrinogen in blood plasma of a patient after stimulation, wherein said patient is in need of such reduction or mitigation, said method comprising administering to the patient a fibrinogen-reducing or mitigating amount of the compound of the formula I

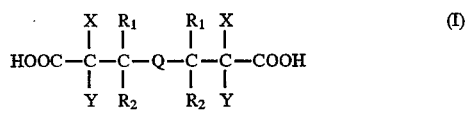

wherein X and Y are both hydrogen, $R_1$ and $R_2$ are both methyl and Q is —$(CH_2)_{10}$—, or X and Y are both chlorine, $R_1$ and $R_2$ are each hydrogen and Q is —$(CH_2)_8$—.

* * * * *